(12) United States Patent
Kapat et al.

(10) Patent No.: US 7,338,202 B1
(45) Date of Patent: Mar. 4, 2008

(54) ULTRA-HIGH TEMPERATURE MICRO-ELECTRO-MECHANICAL SYSTEMS (MEMS)-BASED SENSORS

(75) Inventors: Jayanta S. Kapat, Oviedo, FL (US); Linan An, Oviedo, FL (US); Sanjeev Bharani, Orlando, FL (US)

(73) Assignee: Research Foundation of the University of Central Florida, Orlando, FL (US)

(*) Notice: Subject to any disclaimer, the term of this patent is extended or adjusted under 35 U.S.C. 154(b) by 251 days.

(21) Appl. No.: 10/883,549

(22) Filed: Jul. 1, 2004

Related U.S. Application Data (60) Provisional application No. 60/483,965, filed on Jul. 1, 2003.

(51) Int. Cl.
*G01N 25/40* (2006.01)
*G01K 17/06* (2006.01)
*H01L 21/00* (2006.01)

(52) U.S. Cl. .............................. 374/10; 374/29; 374/39; 438/458

(58) Field of Classification Search ................. 374/29, 374/43, 44, 31, 137, 141, 142, 143, 144, 374/147, 10; 29/592.1, 595; 522/1, 169, 522/172; 427/249.1, 569, 96.1
See application file for complete search history.

(56) References Cited

U.S. PATENT DOCUMENTS

| | | | | |
|---|---|---|---|---|
| 4,131,756 A | | 12/1978 | Smith ........................ 136/230 |
| 4,527,908 A | * | 7/1985 | Arisi ......................... 374/147 |
| 4,576,486 A | | 3/1986 | Dils ........................... 374/131 |
| 5,024,055 A | | 6/1991 | Sato et al. .................. 60/39.27 |
| 5,044,765 A | * | 9/1991 | Noel et al. .................. 374/29 |
| 5,582,485 A | * | 12/1996 | Lesniak ........................ 374/5 |
| 5,730,528 A | * | 3/1998 | Allison et al. ............. 374/161 |
| 6,301,572 B1 | | 10/2001 | Harrison ...................... 706/52 |
| 6,351,999 B1 | | 3/2002 | Maul et al. .............. 73/861.22 |
| 6,367,970 B1 | * | 4/2002 | Danielson .................... 374/43 |
| 6,371,414 B1 | * | 4/2002 | Truax et al. ................ 244/201 |
| 6,394,646 B1 | * | 5/2002 | Ringermacher et al. ....... 374/7 |
| 6,531,341 B1 | | 3/2003 | Peterson et al. ............ 438/123 |

(Continued)

FOREIGN PATENT DOCUMENTS

FR 2660432 A1 * 10/1991

(Continued)

*Primary Examiner*—Gail Verbitsky
(74) *Attorney, Agent, or Firm*—Brian S. Steinberger; Joyce P. Morlin; Law Offices of Brian S. Steinberger, P.A.

(57) ABSTRACT

Novel micro electro mechanical systems (MEMS)-based sensors for use in ultra-high temperature environments are disclosed. The MEMS-based sensors are derived from a class of polymer-derived ceramics selected from the group consisting of SiCN, SiBCN and SiAlCN. The materials of construction are such that, the sensors are capable of accurate, real-time, on-line and in-situ monitoring, suppression of combustion oscillations and detailed measurements in operating structures that have temperatures of from about 1500° K to about 2000° K, extreme pressures/turbulence and harsh chemical off gases. When the novel sensors are mounted on a hot gas path wall, such as, at a combustor exit, there can be a continuous monitoring of pressure pulses/oscillations, wall shear stress, temperature and surface heat flux.

10 Claims, 9 Drawing Sheets

U.S. PATENT DOCUMENTS

| | | | |
|---|---|---|---|
| 6,717,227 B2 | 4/2004 | Tamura et al. | 257/421 |
| 6,840,666 B2 * | 1/2005 | Enachescu et al. | 374/5 |
| 6,919,237 B2 * | 7/2005 | Ohtani et al. | 438/151 |
| 6,974,641 B1 * | 12/2005 | Choy et al. | 428/704 |
| 6,988,826 B2 * | 1/2006 | Zribi et al. | 374/31 |
| 7,087,656 B2 * | 8/2006 | Garcia et al. | 521/63 |
| 2003/0219626 A1 * | 11/2003 | Partee | 428/694 R |
| 2005/0036931 A1 * | 2/2005 | Garcia et al. | 423/345 |
| 2005/0144795 A1 * | 7/2005 | Tanner | 33/366.24 |
| 2005/0169348 A1 * | 8/2005 | Chen et al. | 374/161 |
| 2005/0254547 A1 * | 11/2005 | Zribi et al. | 374/31 |
| 2005/0255233 A1 * | 11/2005 | Madou et al. | 427/96.1 |
| 2006/0018360 A1 * | 1/2006 | Tai et al. | 374/121 |
| 2006/0056959 A1 * | 3/2006 | Sabol et al. | 415/118 |
| 2006/0066006 A1 * | 3/2006 | Haraldsson et al. | 264/255 |
| 2006/0068107 A1 * | 3/2006 | Madou et al. | 427/249.1 |
| 2006/0069176 A1 * | 3/2006 | Bowman et al. | 522/1 |
| 2007/0099791 A1 * | 5/2007 | Wan et al. | 501/88 |

FOREIGN PATENT DOCUMENTS

JP     54158257 A  * 12/1979

* cited by examiner

Side view

Fig. 7A

Top view

Fig. 7B

Side view
Fig. 8A

Top view
Fig. 8B

Cross section
Fig. 9A

Side view
Fig. 9B

Fig. 10

Side view
Fig. 11A

Top view
Fig. 11B

Side view
Fig. 12A

Top view
Fig. 12B

ULTRA-HIGH TEMPERATURE MICRO-ELECTRO-MECHANICAL SYSTEMS (MEMS)-BASED SENSORS

This invention claims the benefit of priority to U.S. Provisional Application 60/483,965 filed on Jul. 1, 2003.

FIELD OF THE INVENTION

This invention relates to smart sensors, in particular to novel micro electro mechanical systems (MEMS)-based sensors for use in harsh, ultra-high temperature environments.

BACKGROUND AND PRIOR ART

Materials technology has had a profound impact on the evolution of human civilization. In the $21^{st}$ century, people are developing smart materials and smart sensors. The class of engineered smart materials based on piezoelectric materials, organic polymers and silicon are useful in micro electro mechanical (MEM) or microelectronic sensors. The engineered smart materials and sensors have the potential for making a major impact on the design and application of structural components and engineering structures, known as "smart structures."

Smart structures are designed to react to the surrounding environment by use of integrated sensors and actuators within the form. Such structures not only can monitor the status of their functioning but also forewarn about the onset of abnormalities and hence impending failures. The smart sensors made of smart materials are to provide in association with other components like actuators and control systems, the required functional capability so as to react to internal and external environments and achieve adaptability. Examples are: smart planes, smart space ships, smart cars, smart bridges and highways, to mention a few. Thus, the fast developing area of smart structure systems is evolving, and an advanced combination of materials, sensors, actuators, control and processing are blended suitably to achieve the end result.

The development of smart materials and sensors has been challenging for some structures, such as gas turbine engines, space craft and the like, because they operate at extreme conditions of temperature, pressure, fluid (air/gaseous mixture, air/fuel mixture) velocity, and the like.

Direct measurement of hot gas properties at the exit of a gas turbine combustor and inlet of the first row of vanes or nozzles under actual operating conditions is quite difficult, if not impossible, with currently available measurement tools. This information is needed both for real-time monitoring so that operation can be optimized as well as for having accurate data for optimized design of downstream components. Temperatures at that location can be in excess of 1800° K, and the chemical conditions are quite hostile, rendering any off-the-shelf intrusive probe quite useless.

Under operating conditions and for accurate measurements, the shroud around this flow path has to be heavily insulated in order to avoid heat loss (which can additionally increase the radial temperature gradient and adversely affect the temperature profile approaching the vanes). Also, because of space and geometric restrictions, and extreme flow conditions, optical windows (for transmitting and receiving optics) are difficult to implement. Typical optical measurement techniques conventionally used for measuring velocity, turbulence, temperature and species, for example, Laser Doppler Velocimeter (LDV), Particle Image Velocimetry (PIV), Coherent Anti-Stokes Raman Scattering (CARS) and Laser Induced Fluorescence (LIF) cannot readily be used without major modifications. As a result, current turbine design primarily relies on estimated or computed data obtained from Computational Fluid Dynamics' (CFD) simulations, the very basis of which is questionable under present experimental conditions. Yet the flow conditions at the combustor exit are very important for turbine design as they form the inlet boundary conditions for turbine design process.

Spectral measurements may be recorded, for example, using equipment such as a paper tablet, computer, compact disc, digital pen, digital video disc, and the like.

Capability for hot flow path measurements for the purpose of better turbine design is even more important for newer power generation concepts such as clean coal technology and Integrated Gasification Combined Cycle (IGCC) plants. Although these concepts have been around for over a decade, there continues to be a need for additional demonstration plants that can provide the necessary performance data to help in optimal design and selective retrofitting.

Human civilization needs sensors that can be integrated into structures that operate in extreme, harsh and hostile environments.

SUMMARY OF THE INVENTION

The first objective of the present invention is to provide a unique series of micro electro mechanical system (MEMS)-based sensors for ultra high temperature applications.

The second objective of the present invention is to provide micro electro mechanical system (MEMS)-based sensors capable of withstanding harsh combusting environments.

The third objective of the present invention is to provide micro electro mechanical systems (MEMS)-based sensors capable of real-time condition monitoring, suppression of combustion oscillations and detailed measurements in an operating gas turbine engine.

The fourth objective of the present invention is to provide micro electro mechanical system (MEMS)-based sensors for point measurements of 3-dimensional velocity, static and stagnation temperature and pressure, turbulence intensity and length scales, wall shear stress, pressure pulsations and wall heat flux in hostile, high temperature flows with direct application to the coal-based power plants, for example, Integrated Gasification Combined Cycle (IGCC) power generators.

The fifth objective of this invention is to provide miniature sensors using polymer-derived ceramics (PDCs) with overall dimensions that enable measurements of greater accuracy.

The sixth objective of this invention is to provide high-temperature sensors for accurate, on-line and in-situ monitoring.

The seventh objective of the invention is to provide micro electro mechanical system (MEMS)-based, ultra-high-temperature, integrated inflow, wall-mounted sensors and optical waveguides for the measurement of temperatures of from about 1500° K to about 2000° K.

The eighth objective of the invention is to provide micro electro mechanical system (MEMS)-based, high temperature sensors that can be mounted on a hot gas path wall, such as, at a combustor exit or turbine inlet and that can continuously monitor pressure pulses/oscillations, wall shear stress, temperature and surface heat flux.

The micro electro mechanical system (MEMS)-based sensors of the present invention are for ultra high temperature applications in gas turbines or other similar systems. In embodiments, the sensors can address the scarcity of (1) high temperature sensors for on-line and in-situ monitoring, and (2) provide detailed experimental data at combustor exit or turbine inlet in an operating gas turbine that is needed for optimized design. The invention demonstrates the use of MEMS-fabricated point sensors for measurement of wall shear, pressure pulses, temperature, heat flux, 3 components of velocity, turbulence intensity and length scale, static and stagnation pressure, and mean and fluctuating temperature for applications in turbine temperatures of from about 1500° K to about 2000° K.

Thus, in embodiments, one main objective of the present invention is to provide smart sensors that are not otherwise available for use in extreme conditions, such as, for example, a gas turbine engine. The sensors are the result of creative and judicious selection of materials, design, fabrication, calibration, flow testing, and material degradation testing. These novel sensors may, for example lead to less down time, less frequent maintenance, better utilization of material, improved safety, information for design optimization, reliability and economy.

Further objects and advantages of this invention will be apparent from the following detailed description of a presently preferred embodiment that is illustrated schematically in the accompanying drawings.

DESCRIPTION OF THE PREFERRED EMBODIMENT

Before explaining the disclosed embodiment of the present invention in detail it is to be understood that the invention is not limited in its application to the details of the particular arrangement shown since the invention is capable of other embodiments. Also, the terminology used herein is for the purpose of description and not of limitation.

It would be useful to discuss the meanings of some words and phrases used herein and their applications before discussing the MEMS-based sensors of the present invention.

A "sensor for sensing point measurements" as used herein refers to a type of sensor and, in particular to one of the six embodiments described herein, used for taking measurements at different points in the flow path of gases and fluids in an engine or other structure operating in ultra high temperature ranges. For example, a measuring point can be in the entrance, middle or exit of an engine and a sensor is placed at the point where it is desirable to take a measurement, thus, the "means for sensing" is a sensor, such as, a thermal anemometer, integrated temperature and heat flux sensor, or dynamic pressure and wall shear sensor placed at a point where it is desirable to take a measurement.

A "sensor for determining flow path conditions" as used herein refers to a type of sensor, and, in particular to one of the four embodiments described herein, used for measuring flow path conditions, such as temperature, velocity, amount of hydrogen in the gas flow, turbulence, pressure and the like. For example, a five-hole probe sensor is placed in a flow path of a gas turbine to measure pressure and velocity of gas flow.

Figure 1:
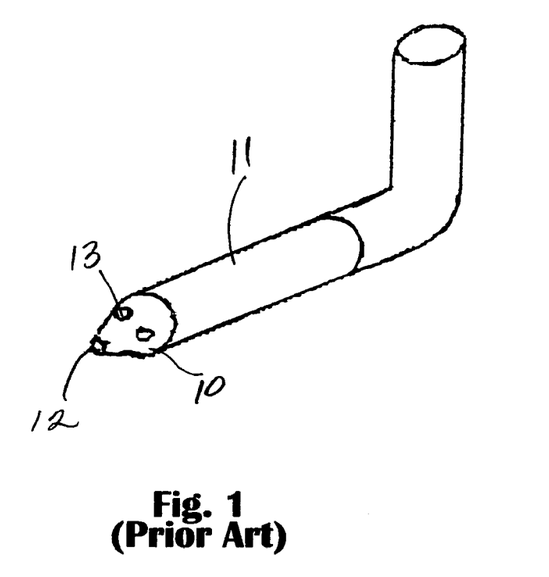
FIG. 1 is a schematic of a conventional five-hole sensor.

FIG. 1 shows a conventional five-hole probe that is a fundamental instrument for measurement of mean velocity components in three-dimensional flows and the data obtained by such a probe is used to validate hot wire ad most of the advanced non-intrusive measurement methods such as, for example, Laser Doppler Velocimetry (LDV) and Particle Image Velocimetry (PIV), and even for validation of Computational Fluid Dynamic (CFD) codes. Such a probe registers pressures at its five holes located at the measuring tip once placed in a flow volume. The five holes are connected to pressure transducers, which in turn can be used to obtain velocity magnitudes and directions. The center tube, when aligned with the major velocity vector gives stagnation pressure while other tubes may, for example, give pseudo-static pressure(s) depending on the type of pressure sensor in use. Apart from the total pressure values, along with the pseudo-static pressure(s) all three vectors of mean velocity as well as the direction can be obtained from the sensor using its calibration curve(s). Basically, flow from a gas turbine is three-dimensional in nature, which requires a rugged and a simple tool to map flow-characteristics in various flow passages. Because the flow path in a turbine is of a complex geometry with narrow dimensions; a sensor with smaller dimensions may be used, for example, to increase the accuracy of measurement data. Typically conventional five-hole sensors are made of steel tubes. They have been found to have limitations in their application to the combusting flow measurements: (1) Being made of metal tubes, even with a provision of cooling, they have a limit in terms of temperature to withstand in a hostile, high temperature, combusting environment, (2) Conventional designs are not suitable for measurements in narrow complex flow passages where precise measurement is required.

The present invention overcomes the second limitation using the similar planar geometry as explained in more detail below; newly developed polymer-derived ceramics overcome the first limitation. A simplified design has been proposed by Babinsky, et al. that uses a cylindrical sensor having five holes at its flat tip with a provision of passive fence to separate each hole and to give directional sensitivity.

Figure 2:
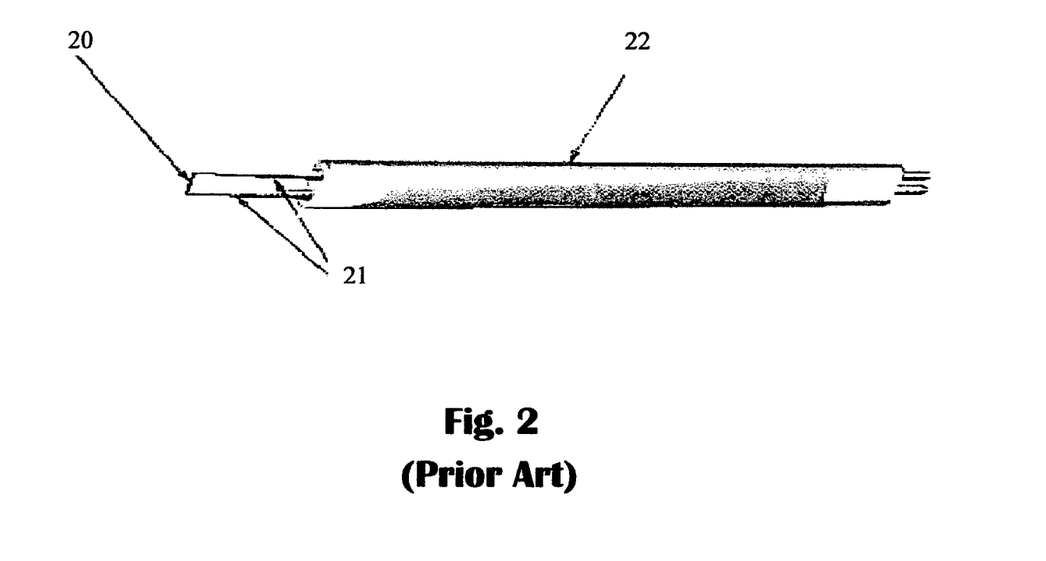
FIG. 2 shows a typical conventional hot-wire sensor.

The hotwire sensor is widely used in the experimental fluid dynamic research area. It works on the principle of convective heat transfer from its heated sensing element. The most common sensor configurations are cylindrical hotwires as shown in FIG. 2.

The heat transfer from a heated element 20 (wire sensor) placed in a fluid flow depends on both the properties of the ambient fluid and the flow parameters. They have excellent frequency response at up to about 400 kHz. In conventional instruments the sensor wire is made of tungsten or platinum. The most common application is constant temperature mode in which velocity can be determined. Another example is in constant current mode which allows the sensor to be used as a resistance temperature detector (RTD) for temperature detection.

The prongs 21 (support needles) on which the sensor 22 is welded or soldered have much higher conductivity as compared to the sensor in order to minimize additional resistance in the sensor circuit. The value of temperature sensitivity of electrical resistance for typical sensor materials are: Platinum=$3.5 \times 10^{-3}$(° C.)$^{-1}$ and Tungsten=$5.2 \times 10^{-3}$(° C.)$^{-1}$. All other sensors are quite standard. Pressure and shear stress sensors utilize piezo-restive property of the proposed amorphous material. All temperature sensors utilize temperature dependence of resistance as will be shown later.

Figure 3:
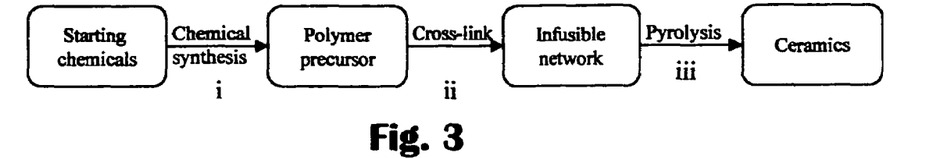
FIG. 3 is a flow diagram of basic steps for preparing polymer-derived ceramics.

The present invention uses recently developed polymer-derived ceramics to fabricate all sensors. This new class of materials is synthesized by thermal decomposition of polymer precursors with the procedure shown in FIG. 3: (i) synthesize or modify polymer precursors, (ii) shape and cross-link to form infusible polymer components, and (iii) convert the polymer component to a ceramic by pyrolysis at from about 800 to about 1200° C. The materials thus obtained are predominantly amorphous alloys, consisting of silicon, carbon and nitrogen; other elements such as boron and aluminum can also be incorporated into the network for the modifying and improving physical, chemical and electrical properties.

Figure 4:
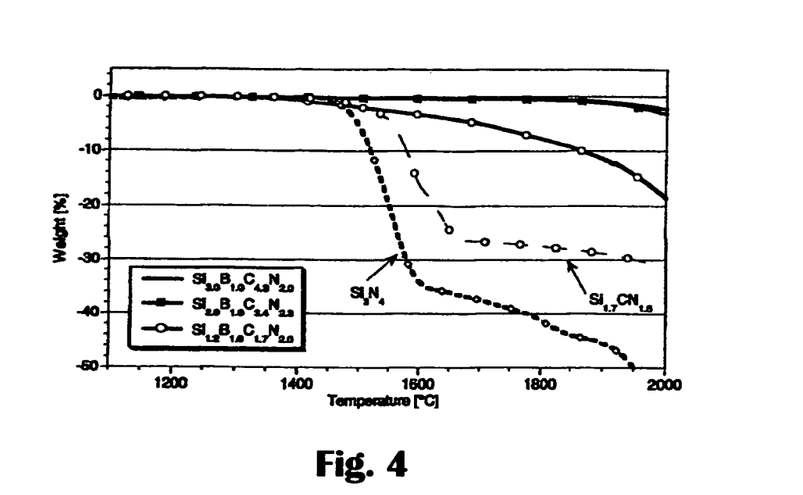
FIG. 4 shows the thermal gravimetric analysis (TGA) of various SiBCN materials compared with SiCN and commercial silicon nitride.

The polymer-derived ceramics (PDCs) are particularly suitable for the proposed applications due to the following unique features:

First, the PDCs have excellent thermo-mechanical properties at high temperatures. While synthesized at relatively low temperatures, the polymer-derived ceramics exhibited excellent high temperature properties: they resist thermal decomposition and large-scale crystallization up to about 1800° C.; their high temperature oxidation and creep resistance is even better than the state-of-the-art SiC and $Si_3N_4$. FIG. 4 is thermal gravimetric analysis (TGA) data for several PDCs, together with polycrystalline $Si_3N_4$, indicating the SiBCN is stable up to about 1800° C. Table 1 shows some physical-mechanical properties of PDCs as compared to the other ceramics (SiC, $Si_3N_4$). Note that the PDCs possess much better thermal shock resistance. Due to the absence of grain boundary phases, it is expected that such excellent mechanical behavior can be retained at high temperature. These excellent thermo-mechanical properties suggest that the PDCs are suitable for high temperature applications.

TABLE 1

Properties of polymer derived SiCN and other high temperature materials

| Properties | PDC-SiCN | SiC | $Si_3N_4$ |
|---|---|---|---|
| Density (g/cm$^3$) | 2.3 | 3.17 | 3.19 |
| Young's modulus (GPa) | 150 | 400 | 320 |
| CTE ($\times 10^{-6}$/K) | 3 | 3.8 | 2.5 |
| Strength (MPa) | ~1000 | 420 | 700 |
| Hardness (GPa) | 20 | 30 | 28 |
| Thermal Shock FOM* | 2200 | 250 | 880 |

*Thermal shock FOM = strength/(E-modulus.CTE)

Figure 5:
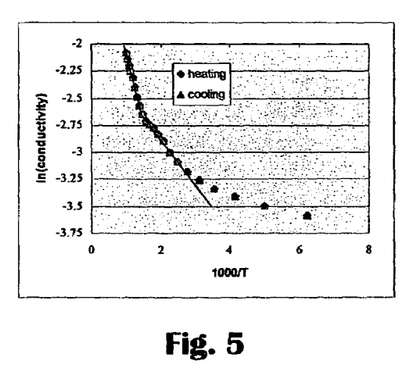
FIG. 5 shows the electric conductivity of SiAlCN as a function of temperature.

Another advantage of the PDCs of the present invention is tunable electric conductivity. The PDCs exhibit semiconductor behavior and their conductivities can be tailored in a large range: from insulator ($10^{-8}$ ($\Omega$.cm)$^{-1}$) to semiconductor ($10^4$ ($\Omega$.cm)$^{-1}$). FIG. 5 shows the conductivity of the SiAlCN as a function of temperature up to about 1000° C., which suggests that the SiAlCN material shows typical amorphous semiconductor behavior:

(i) At temperatures lower than about 360° C., the conductivity follows variable range hopping mechanism as derived by Mott [14]:

$$\sigma_{dc}(T) \sim \exp\left(-\frac{T_o}{T^{1/4}}\right)$$

(ii) In temperature range of 360-680° C., the conductivity is associated with tunneling of charge carries between excited states:

$$\sigma_{dc}(T) \sim \exp\left(-\frac{B_1}{T}\right)$$

where $B_1$ is a constant ~1500° K and is to be determined through measurement (iii) At temperatures higher than 680° C., the conductivity is controlled by the excitation of charge carries into the conduction band:

$$\sigma_{dc}(T) \sim \exp\left(-\frac{B_2}{T}\right),$$

where $B_2$ is ~3000° K and is to be determined.

The sensitivity of proposed temperature and hotwire sensors depends on temperature coefficient of resistivity of the sensing material, which can be calculated by:

$$\alpha = \frac{\partial R}{R \partial T} = \frac{B}{T^2}.$$

For SiAlCN, $\alpha$ is $4\times10^{-3}$ at 600° K, $3\times10^{-3}$ at 1000° K and $1.3\times10^{-3}$ at 1500° K: in the same range with metal materials (such as Pt, $\alpha=3\times10^{-3}$), It can also be seen that the conductivity of this material is perfectly repeatable during heating/cooling cycles up to approximately 1000° C., suggesting that the sensors made from the SiAlCN can be repeatedly used to high temperatures.

Figure 6:
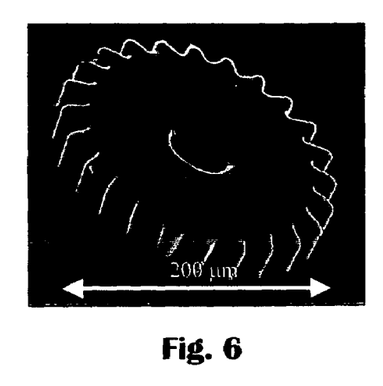
FIG. 6 shows a scanning electron microscope (SEM) micrograph of SiCN micro-gear of 200 μm diameter and 40 μm thickness.

Processability is made easier in embodiments of the PDCs disclosed in this invention. Due to the "glass-transition" temperature of the cross-linked polymer usually being greater than the pyrolysis temperature, the shapes formed in the plastic state are retained in the ceramic state. This leads to a flexible and cost-efficient approach to manufacture ceramic components and devices from these interesting materials. For example, the component can be shaped or formed in the organic form, just prior to pyrolysis, which will yield self-similar ceramic components upon pyrolysis. It is possible to fabricate high temperature fibers, protection coatings, and ceramic matrix composites. Most recently, the micro-fabrication techniques have been developed to fabricate ceramic by this unique material. FIG. 6 shows the scanning electron microscope (SEM) micrograph of SiCN ceramic micro-gear made by micro-casting technique.

Thus, a family of novel high temperature sensors fabricated from PDCs are now available, for example, for gas turbine applications. These sensors can make point measurements of 3 components of velocity with turbulence intensity and length scales, static and stagnation temperature (along with its fluctuations) and pressure, wall shear stress, pressure and heat flux, pressure pulses (as caused by combustion), major and minor species concentration. The sensors are able to withstand harsh turbine conditions up to 2000° K. These sensors can contribute to research, design and operation of gas turbines through (1) continuous real-time monitoring for combustion stability, occurrence of hot spots, and pollutant production, (2) detailed maps of 3 components of velocity, pressure, fluctuating and mean temperature, turbulence intensity and length scale and species concentration at the combustor exit, inside the transition pieces or inlet to the first row of vanes.

No such sensor exists at present that can match the high temperature performance of the PDC sensors without any external cooling. Thus, PDC sensors can facilitate a tremendous leap forward in the gas turbine industry as well as for understanding of the complex science that governs the flow field between and inside combustor and turbine. For example, accurate measurement of turbulence intensity and length scale at the combustor exit has been unavailable, whereas information is quite valuable in downstream turbine design.

A series of in-flow, wall-mounted and optical sensors for flow variables and concentration of major and minor species is designed. A demonstration project involving a gas turbine is one embodiment of the invention that verifies or validates the key enabling concepts of the overall sensor system.

Referring now to the design of the PDC sensors, which follows the basic principles of aerodynamics and heat transfer as applicable to the high temperature environment of a gas turbine. Each of the following designs optimize the respective sensor dimensions based on material properties so as to maximize the corresponding sensor sensitivity.

Figure 7A:
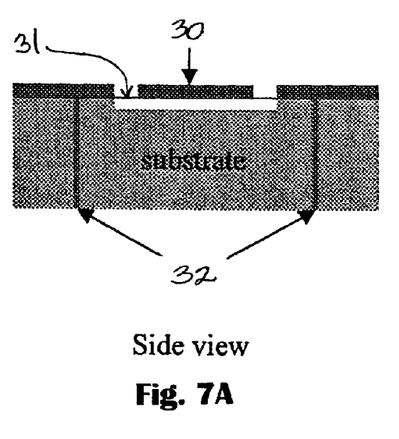
FIG. 7A shows a side view of a floating element shear sensor for mounting on a wall.
Figure 7B:
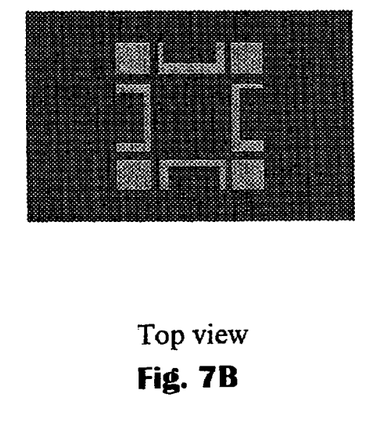
FIG. 7B shows a top view of a floating element shear sensor for mounting on a wall.

As a first embodiment of the present invention, a wall shear sensor, also known as a floating element shear sensor, is shown in FIG. 7A. The design consists of a floating plate or element 30, eight tethers 31 and conducting wires 32 for connection. Four of the tethers sense any movement in the floating element due to side-to-side shear and the other four tethers sense any movement due to up-down shear. See the top view shown in FIG. 7B. The tethers work as mechanical supports for the plate as well as piezo-resistive resistors in the sensing-transduction scheme. For measurement shear in any direction, two of the four shear experience tension and the other two compression. Because of the piezo-resistive property of the material, the resistance of each tether changes under tension or compression, and this change in resistance is measured through a half-bridge configuration (as in strain gauges). A half-bridging electrical configuration assuming matched resistance, the output, $\Delta V$, is given by $$\Delta V = \frac{V_A G A_P}{8 A_T E} \tau$$

where $V_A$ is applied voltage, G the gauge factor, $A_P$ the area of the plate, $A_t$ the cross-section area of the tether, E Young's modulus, and $\tau$ the shear stress to be measured. By measuring shear in two orthoganal directions (with the help of eight tethers) the direction of shear stress can be resolved. Through an array of this sensor, mounted around the circumference at the combustor exit, near wall flow-pulsation can be detected, which is very important for monitoring of combustion stability.

Figure 8A:
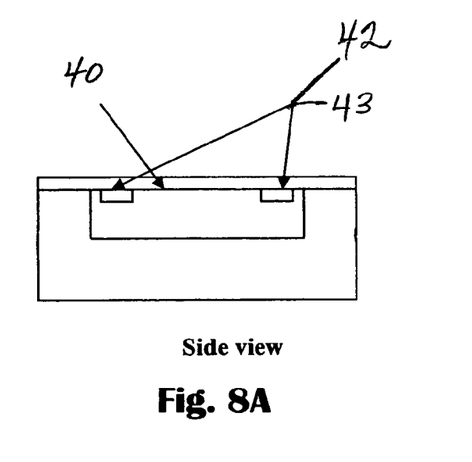
FIG. 8A shows a side view of a wall pressure sensor.
Figure 8B:
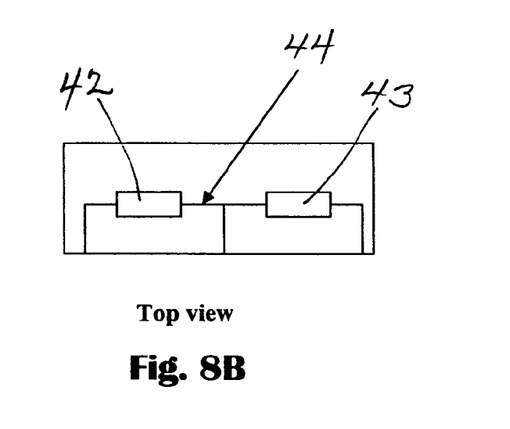
FIG. 8B shows a top view of a wall pressure sensor.

A second embodiment, a wall pressure sensor, technically known as a simple piezo-resistive pressure sensor, is shown in FIGS. 8A and 8B. As in the wall shear sensors, the piezo resistive property of the base material is the key enabling factor for this ultra-high temperature sensor. Piezo resistive pressure sensor consists of a diaphragm 40, a sealed cavity 41, two piezo resistive strain gauges 42, 43 and conducting connections 44. Another two unloaded strain gauges would be mounted inside the sealed cavity so that they do experience any strain, but do experience the same environmental conditions. These latter two gauges 42, 43 will act as compensators, and all four gauges will operate on a full bridge circuit. Through an array of sensors mounted around the circumference at the combustor exit, pressure pulses can be detected, which is important for monitoring of combustion stability.

Figure 9A:
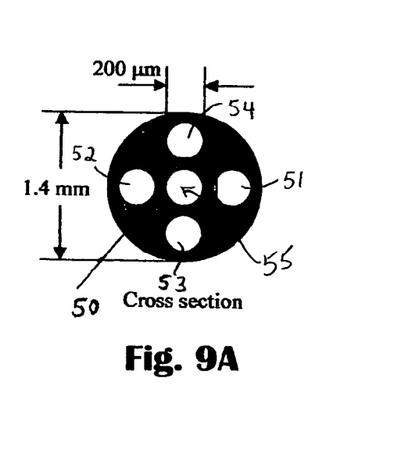
FIG. 9A is a cross-sectional schematic of a five-hole sensor.
Figure 9B:
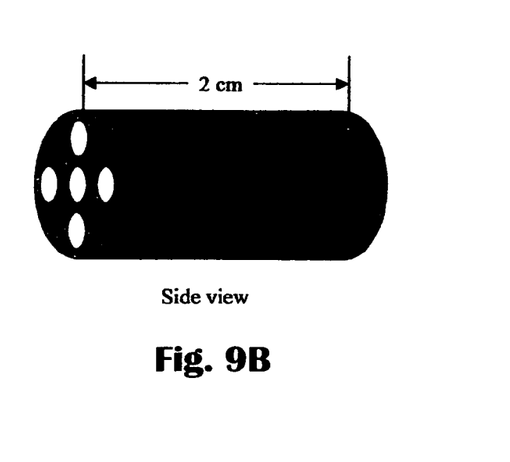
FIG. 9B is a side view schematic of a five-hole sensor.

As a third embodiment, the design for a five-hole probe is shown in FIGS. 9A and 9B. A basic, conventional design of a five-hole sensor as described early and shown in FIG. 1, is modified with the inclusion of tip fences. The fences 50 have a conical side view and are described in more details under fabrication. The fences 50 allow the adaptation of ceramic micro-fabrication for the five-hole probe sensor.

Two side holes 51, 52 provide the yaw angle of the velocity vector, whereas holes above 54 and below 53 the center one 55 provide the pitch angle. All five holes provide together static and stagnation pressures. The design would involve determining all relevant dimensions so that no adverse aerodynamic effect is felt at the measurement tip. The hole and sensor diameters are subject to micro-fabrication limitations, and the frequency response needed. In this design, only mean value of velocity and pressures would be sought with the help of this probe.

Figure 10:
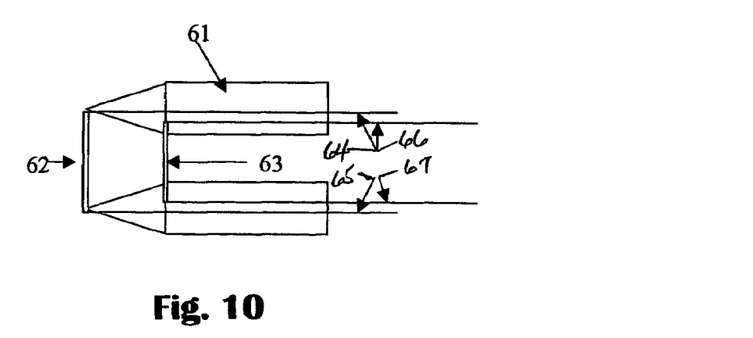
FIG. 10 is a schematic of a hotwire sensor with temperature sensor.

FIG. 10 shows a design for a fourth embodiment of the present invention, an integrated hot-wire/RTD sensor for measuring mean and fluctuating velocity and temperature. The design is based on traditional hot-wire and resistance temperature detector (RTD) designs, where the sensing wires have a 2 to 4 orders of magnitude larger electrical resistance than connecting wires. The sensing wires must have a strong dependency of electrical resistivity on temperature, which is exploited, through the use of a Wheatstone bridge, to measure velocity and temperature values, including their high frequency fluctuations. The size of the wires and the bridge circuit determine the spatial and temporal resolution of the sensors. Since the resistance values of the sensors are different from conventional sensors, the bridge circuits have to be custom designed. In FIG. 10, two supporting needles 60, 61 are connected at the needle end by a hotwire sensor 62 and at a point where the needles begin to taper, a resistance temperature detector (RTD) sensor 63 connects the two supporting needles. Conductive wires 64 and 65 are connected by parallel lines to hotwire sensor 62. Conductive wires 66 and 67 are connected in parallel lines to RTD sensor 63 to complete the design.

Figure 11A:
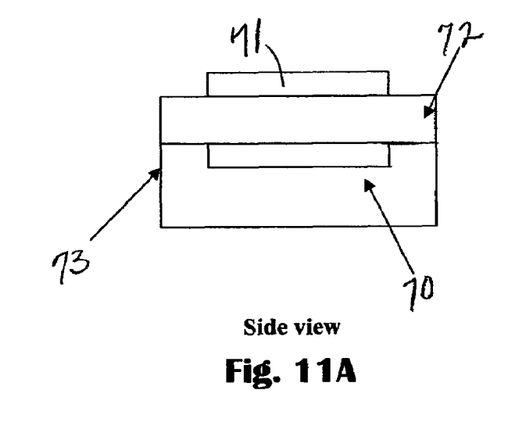
FIG. 11A is a side view schematic of an integrated temperature/heat flux sensor.
Figure 11B:
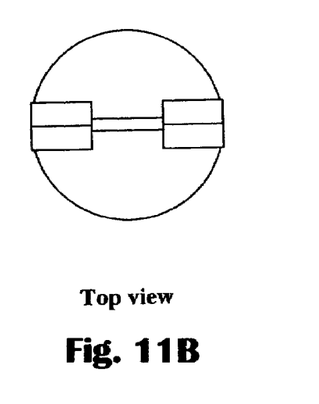
FIG. 11B is a top view schematic of an integrated temperature/heat flux sensor.

A fifth embodiment of the present invention is an integrated temperature/heat flux sensor shown in FIGS. 11A and 11B. This sensor is based on the principle of resistance temperature detector (RTD) sensors discussed above. Two RTD sensors 70 and 71 are used with an electrically insulating PDC with low thermal conductivity 72, and conducting lead 73. By measuring the temperatures with the two RTD sensors and by knowing the properties of the in-between (green) PDC, one can calculate heat flux by Fourier's law. The backside electrical insulation with high thermal conductivity ensures that thermal path is not impeded in the presence of the sensor.

A sixth embodiment of the micro electro mechanical sensors of the present invention is as an Optical Waveguide.

Figure 12A:
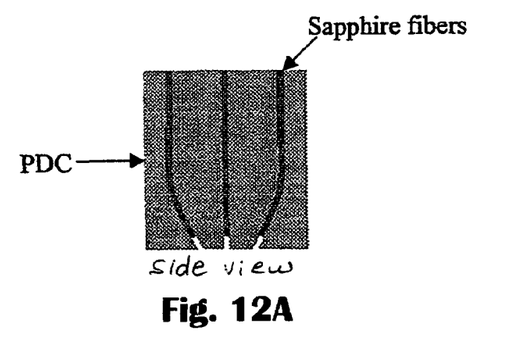
FIG. 12A is a side view schematic of proposed waveguide bundle for Laser Doppler Velocimetry (LDV), Coherent Anti-Stokes Raman Scattering (CARS), and Laser Induced Fluorescence (LIF) applications.
Figure 12B:
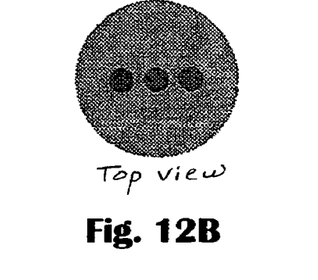
FIG. 12B is a top view schematic of proposed waveguide bundle for Laser Doppler Velocimetry (LDV), Coherent Anti-Stokes Raman Scattering (CARS), and Laser Induced Fluorescence (LIF) applications.
Figure 13:
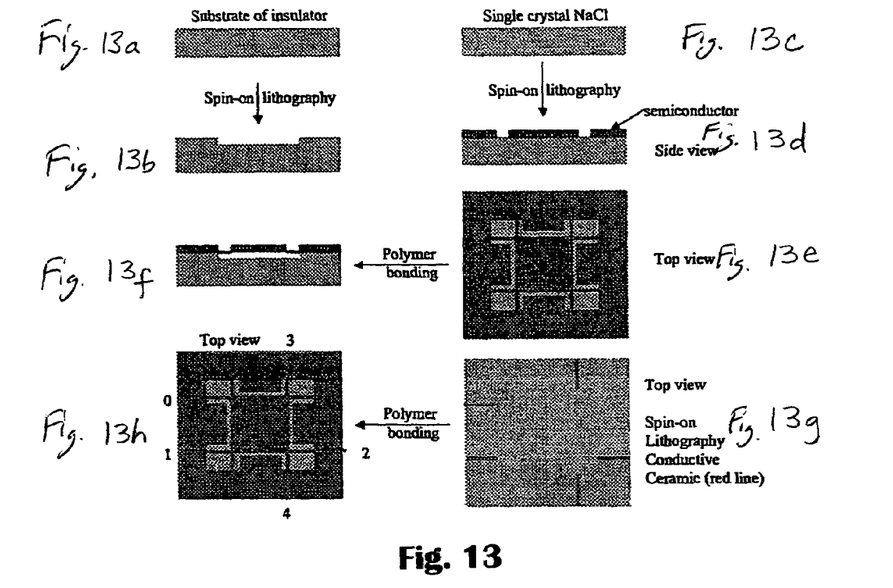
FIGS. 13a, 13b, 13c, 13d, 13e, 13f, 13g, 13h show the fabrication procedure of a floating element shear sensor.
Figure 14:
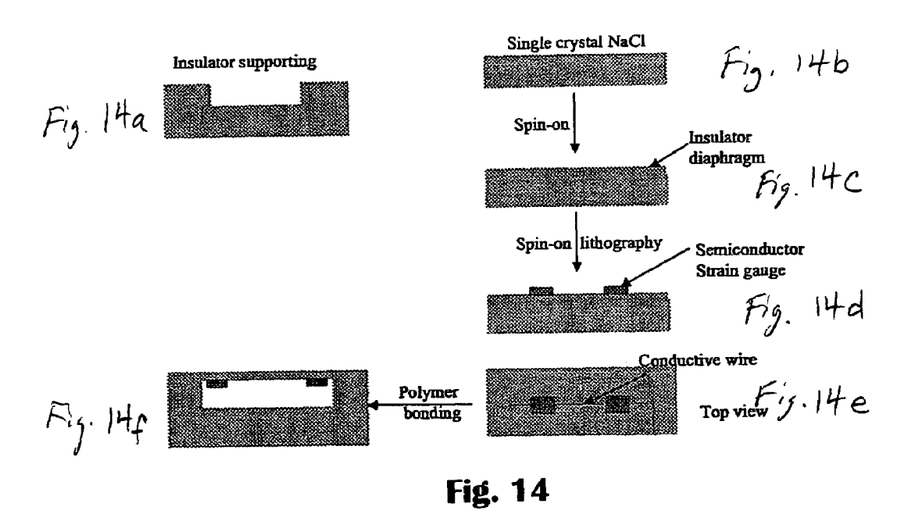
FIGS. 14a, 14b, 14c, 14d, 14e, 14f show the fabrication procedure for pressure sensor.
Figure 15:
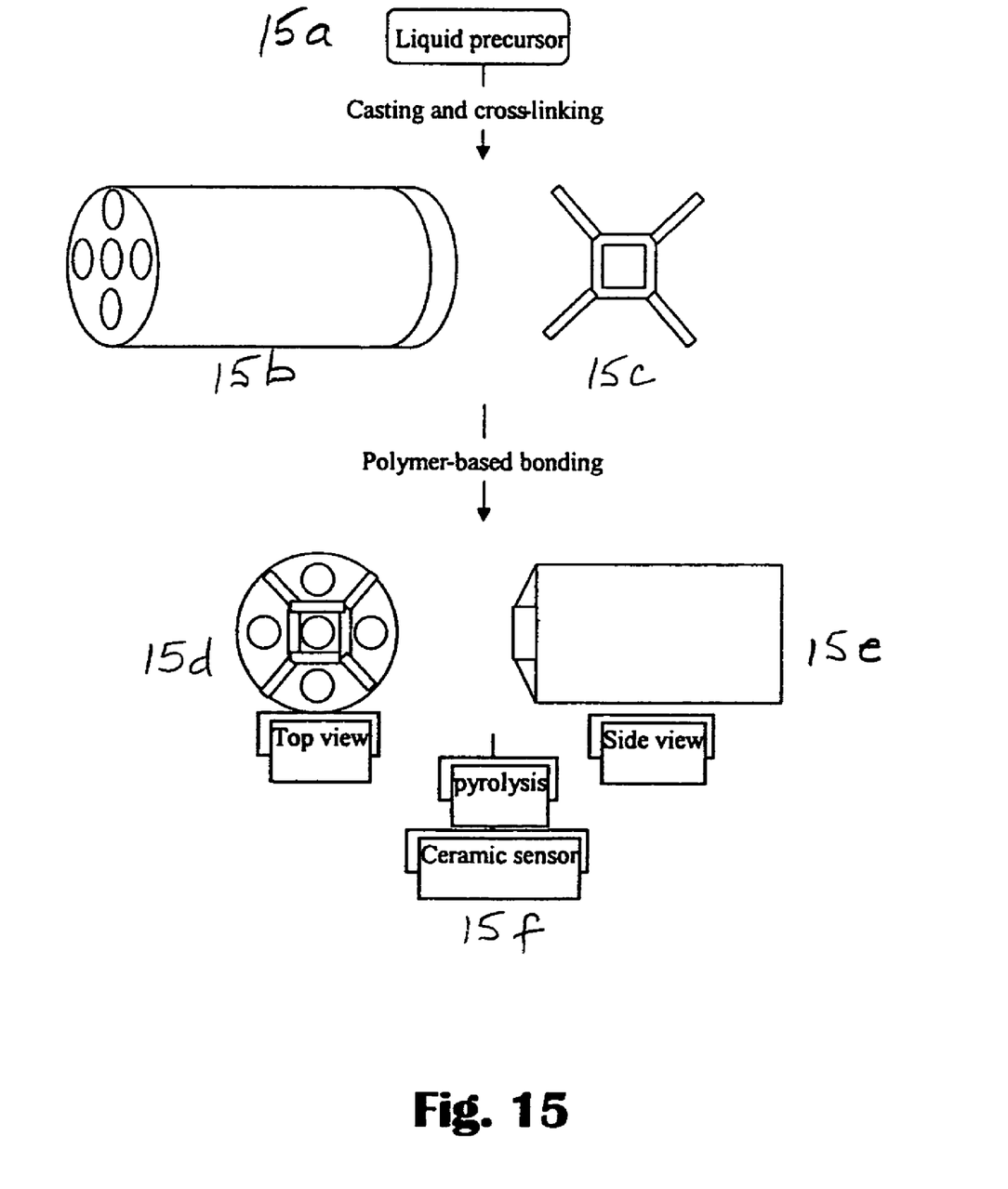
FIGS. 15a, 15b, 15c, 15d, 15e, 15f are schematic illustrations of the fabrication procedure of a five-hole probe.

Optical techniques such as laser Doppler technique for velocity measurements, spontaneous Raman measurements of temperature and major species concentration and laser induced fluorescence technique for minor species measurement require high temperature waveguide in a practical application. Even though having an optical signal coming in through optical windows in the shroud could use these techniques, receiving and transmitting signals should be enclosed in waveguides until close to the measurement section so that the beam steering line-of-sight averaging in hot environment can be avoided. Sapphire is an excellent optical waveguide for high temperature applications. However, the fine fiber is very fragile and bulk material is quite expensive. Hence sapphire waveguides can be enclosed inside PDC structural shells for use in the harsh environment of a turbine. FIGS. 12A and 12B show a schematic waveguide bundle of sapphire fibers.

The polymer-derived ceramics (PDCs) are critical to the development of smart sensors for high temperature applications. Thus, material optimization and property characterization for SiAlCN, SiBCN or SiCN-based polymer-based ceramics are presented. SiAlCN, SiBCN and SiCN-based polymer-based ceramics are examples of the materials used for fabrication of different portions of the sensors.

Electrical properties of the PDCs were characterized. To optimize the properties of SiAlCN for oxidation and corrosion resistance at higher temperatures for structural members, to optimize SiCN material for isolating support leads and to optimize SiAlCN for the purpose of sensing as well as connecting, the supporting needles will be such that they have high electrical resistance, while the sensing wires are to be conductive. The following three classes of materials are used in this research:

Class 1: SiCN is derived from poly[hydazinomethylsilane] and has been known to exhibit conductivity up to $10^4$ $(\Omega.cm)^{-1}$.

Class 2: SiAlCN exhibits amorphous semiconductor behavior. Its conductivity as a function of temperature varies over a wide range and is used in the wall pressure sensor shown in FIGS. 8A and 8B. This material also exhibits excellent oxidation resistance.

Class 3: SiCN is derived from polysilazane (NCP-200). Even though this material has similar composition with Class 1 materials, it is an electrical insulator.

Poly[hydazinomethylsilane] precursor for class 1 material is synthesized by reaction of methyldichlorosailane with hydrazine ($NH_2NH_2$). The reaction is described as following:

$$2Me_2SiHCl + NH_2NH_2 \rightarrow Me_2SiNHNHSiMe_2 + 2\ HCl$$

The precursor for class 2 material is synthesized by reacting a polysilazane, commercially available as Kion Ceraset® manufactured by the Kion Corporation, Huntingdon Valley, Pa., with $Al(CH_3)_3$. The Al content in the final ceramics can be tailored by varying the ratio of the two chemicals. The precursor for Class 3 material, NCP-200, is commercially available. All bulk samples are prepared from the three precursors by cross-linking and pyrolysis, as discussed in more detail below. The conductivity of the Class 1 and 2 materials as a function of temperatures up to 1400° C. indicates that the conductivity of the material decreases with increasing temperature. The focus on the effect of Al content on the conductivity is important to optimize the sensor design. The resistance properties may be tailored to the specific application by varying the process parameters. High temperature mechanical behavior such as creep and high temperature strength of the three materials are conducted at temperatures up to 1400° C.

PDCs are also studied to characterize environmental resistance. As a class of materials, PDCs must have appropriate resistance against degradation in the presence of water vapor, for all cases, and sulfur, for syngas combustion. A recent breakthrough in this class of material has tremendously increased its resistance to water vapor. However, further testing is required. Additional testing is performed to characterize the material resistance in the presence of sulfur under simulated syngas combustion environment.

With regard to sensor fabrication, fabrication methodology for various sensor components was optimized such that the required dimensional details and property values can be satisfied.

The fabrication of a Micro Floating Element Shear Sensor (embodiment one) is schematically shown in FIGS. 13a, 13b, 13c, 13d, 13e, 13f, 13g, and 13h. The techniques such as casting, lithography and polymer-based bonding are well documented and can be found Am. Ceram. Soc. Bull. 80 (5), 25-30, (2001) and is incorporated herein by reference. First, the substrate will be made from a polymer precursor that results in the insulator ceramic by casting the precursor. The surface of the substrate is polished to 0.25 μm finish. The thin layer of insulator precursor is then spin-on coated on the surface of substrate and patterned using lithography technique. The single crystal NaCl will be used as "handle wafer". The semiconductor precursor will be spin-on coated on the NaCl single crystal surface, which can be polished to nano-scale, and then patterned using lithography to form a floating element. The obtained floating element will then be bonded to the insulator substrate. The structure can be easily released from NaCi crystal by immersing into water for 5 seconds. The conducting wire will be fabricated on NaCl surface in a similar manner, and then bonded on the top of the floating element. Finally, the polymer structure will be converted to a ceramic sensor by pyrolysis at 1100° C. under argon (Ar).

The fabrication of Micro Pressure Sensor (embodiment two) is schematically shown in FIGS. 14a, 14b, 14c, 14d, 14e, and 14f. First, the casting polymer precursor that results in the insulator makes the insulator supporting structure ceramic. Again the single crystal NaCl will be used as "handle wafer". The thin layer of insulator precursor is spun-on the surface of NaCl to form a diaphragm. The semiconductor precursor is then spin-on coated on the top of an insulator diaphragm and then patterned using lithography. The conducting wire will be fabricated in a similar manner. The diaphragm layer is then bonded to the supporting structure. Finally, the polymer structure is converted to a ceramic sensor by pyrolysis at 1100° C. under argon (Ar).

Fabrication of the third embodiment, a flow/pressure sensor, consisting of a five-hole sensor and passive fence, is shown in FIGS. 15a, 15b, 15c, 15d, 15e, and 15f. This kind of sensor requires that the materials possess, among other properties, high stiffness and corrosion/oxidation resistance. Class 2—SiAlCN ceramics are used to fabricate this type of sensor since this material shows excellent oxidation and corrosion resistance at high temperature. The techniques such as casting and polymer-based bonding are known by those skilled in the art. First, the five-hole cylindrical sensor with flat tip and passive fence will be fabricated separately by casting the liquid precursor of the mixture of Ceraset and aluminum isopropyloxide and cross-linking. The obtained cross-linked polymer parts will then be bonded together by using the same liquid precursor as adhesive. Finally, the bonded sensor will be converted to a ceramic sensor by pyrolysis at 1100° C.

Figure 16:
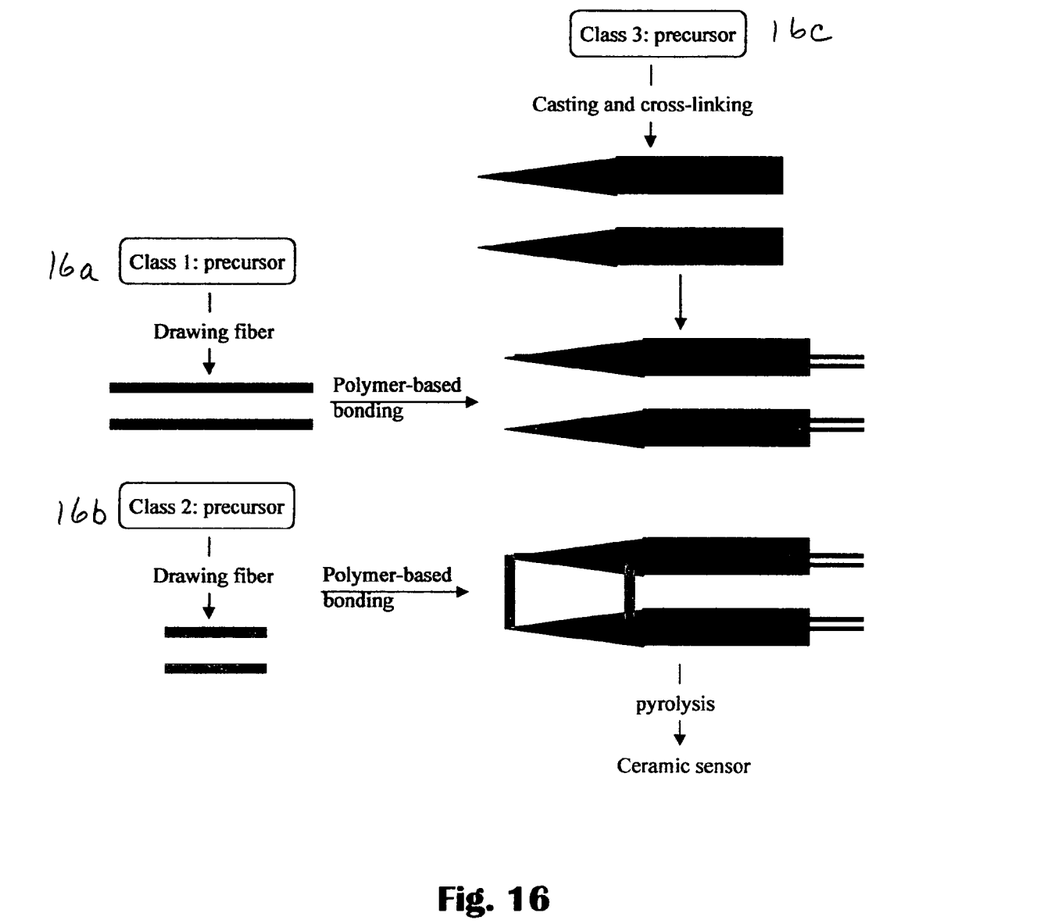
FIGS. 16a, 16b, 16c are schematic illustrations of the fabrication procedure of a hot-wire/RTD sensor.
Figure 17:
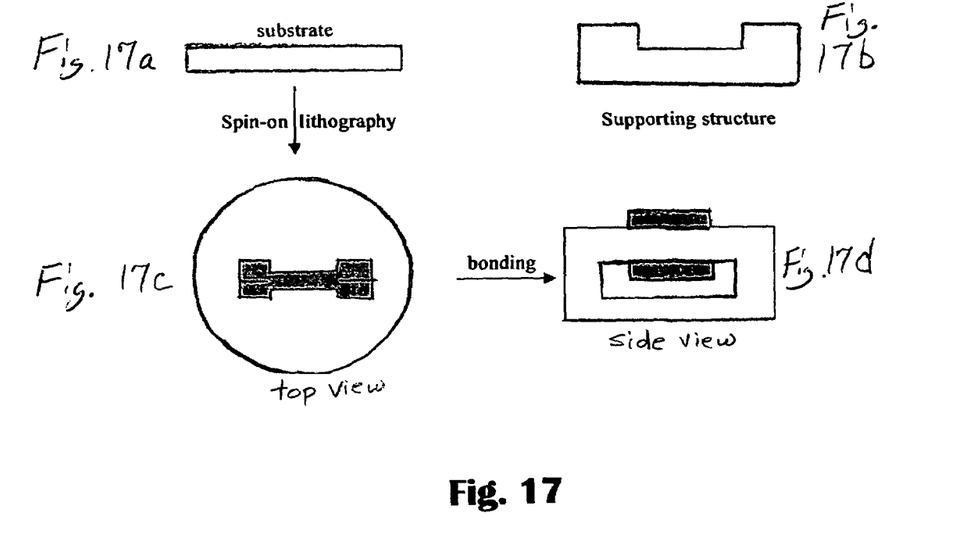
FIGS. 17a, 17b, 17c, 17d show the fabrication procedure for temperature/heat flux sensor.

The geometry of the hotwire/RTD sensor (embodiment four), consisting of hot-wires, supporting needles and conductive wires, is shown in FIGS. 16a, 16b, and 16c. This kind of sensor requires that the support needles be insulators; sensor wires possess medium conductivity; and the connecting wires possess high conductivity. The ratio of electric resistances of sensors to conductors should be ~1000 to minimize loading error. Class 3—SiCN ceramics are used to fabricate the support needles since it has high resistivity, Class 2—SiAlCN ceramic to fabricate sensors since it has relatively low conductivity ($10^{-1}$ ($\Omega$.cm)$^{-1}$), and Class 1 material to fabricate connectors since it has high conductivity ($10^{4}$ ($\Omega$.cm)$^{-1}$).

Reference is now made to the fabrication technologies schematically shown in FIGS. 16a, 16b and 16c. First, the support needles are fabricated by casting and cross-linking of Class 3 precursor; hotwires and conducive wires are fabricated by drawing the fibers from Class 2 and class 1 precursors, respectively. The diameter of the fibers can be controlled from 100 μm to 500 μm, depending on the design. The obtained conductive wires are then bonded to support needles using polymer based bonding. The hotwires are then bonded to conductive wires. Finally, the bonded sensor is converted to a ceramic sensor by pyrolysis.

The fabrication technologies for a temperature/heat flux sensor (embodiment five) are schematically shown in FIGS. 17a, 17b, 17c and 17d. First, the substrate and supporting structure are made from a polymer precursor that results in the insulator ceramic by cross-linking the precursor. The surface of the substrate is polished to 0.25 μm finish. The thin layer of semiconductor precursor is spin-on coated and patterned on both sides of the substrate. The conducting wire will be fabricated by the similar way. The substrate is then bonded to a supporting structure. Finally, the polymer structure will be converted to ceramic sensor by pyrolysis at 1100° C. under argon (Ar).

Figure 18:
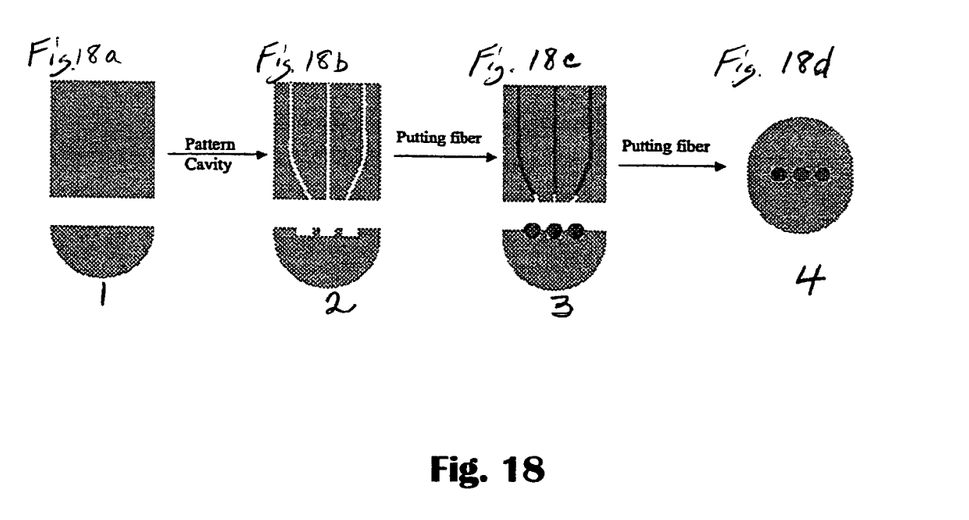
FIGS. 18a, 18b, 18c, 18d are schematic illustrations of the fabrication of an optical waveguide.

Fabrication of an optical waveguide (embodiment six) is shown in FIGS. 18a, 18b, 18c and 18d. First, two half cylinders are made by the casting the polymer precursor as illustrated in step (1) shown in FIG. 18a. The layer of precursor is spin-on coated on the flat surface of each cylinder, and then patterned to form cavities as shown in step (2), FIG. 18b. The sapphire fibers will then be put into the cavities (steps 3 and 4); FIGS. 18c and 18d. The two half cylinders will then be bonded together. The whole structure will then be pyrolyzed to form ceramics. The sizes of the cavities need to be carefully designed so that the size of cavities after pyrolysis will be similar to the diameter of the fiber after shrinkage, avoiding large stress on the fibers.

After material testing and sensor fabrication, flow calibration of sensors in a wind tunnel can be conducted.

The calibration of a five-hole sensor was carried out in an existing wind tunnel. The tunnel is designed for controllable, low to high turbulence intensity with a uniform flow condition in the test section where the flow temperatures can be controlled up to 350K. Low temperature calibration is performed in combinations with high temperature material degradation. The newly developed five-hole sensor is calibrated by putting it in a test section of the calibration wind tunnel along with a standard Pitot-static probe. The five-hole sensor will be attached to a specially designed probe-holder which can provide controlled yaw and pitch movement in the range of +30° to −30° in increments of 1.0°.

Calibration of the five-hole sensor is carried out in the null mode, i.e. by rotating the probe about its stem axis until pressure values at the two side holes are equalized. The pressure values at all the holes are noted down using a Scanivalve pressure scanner (least count 0.01 mm of water) in order to derive calibration coefficients for the assessment of yaw, pitch, mean velocity and pressure values as given below:

$$K_2 = \frac{(p_4 - p_2)}{q}, K_{pt} = \frac{(p_t - p_c)}{q}, K_{dyn} = \frac{(p_c - p_m)}{q},$$

where $$p_m \frac{(p_1 + p_2 + p_3 + p_4)}{4}$$

and $p_t$ is the total pressure.

In order to perform the flow calibration of the hotwire/RTD sensor, the same wind tunnel as used for the five-hole sensor is used. The hotwire probe will be mounted in the test-section such that the sensing wires are perpendicular to the flow direction in the test section. A standard Pitot-static probe is also fixed with its sensing tip parallel to the flow direction so that both probes experience the same flow magnitude. First calibration is carried out in cold flow in a velocity range of 5 to 60 m/s, and then warm flow calibrations will be performed at temperatures up to approximately 350K. The sensors are connected to two standard Wheatstone bridge circuits so as to receive the anemometer and RTD signals. The velocity sensor are operated in constant temperature mode while the temperature sensor is operated in the constant current mode, as done with the conventional probes. The King's law is used to relate Pitot-static probes derived velocity magnitudes with the emf from the corresponding anemometer set as given: $E^2=A+BU^n$, where A represents the emf which is obtained when the probe is facing zero velocity condition. Exponent 'n' will be found from the calibration data/curve.

With regard to the flow calibration of all other sensors, which does not include the optical waveguide, as it is not a self-standing sensor, these calibrations are performed in the same wind-tunnel against standard, NIST-traceable calibration standards.

In order to record structural deformation, degradation, if any, of the sensor materials in a high temperature environment, further testing was needed as discussed below.

Materials degradation due to interaction with air and steam in high temperature is examined to provide critical information necessary for sensor applications. Degradation of SiAlCN is examined under an air oxidation and pure steam oxidation environment at temperatures of 1100C, 1200C and 1300C, representing operating temperatures of advanced turbine engines. Some of the critical materials properties examined as a function of high temperature exposure include: (1) Degradation of surface geometry and dimensional stability due to oxidation/hot corrosion, (2) Changes in electrical conductivity as a function of surface degradation and phase transformations (i.e., crystallization) in SiAlCN.

SiAlCN-based sensors are found to be capable and durable. Also, changes in properties that influence the output sensor data to be analyzed for the evaluation of turbine operation are excellent.

To simulate materials degradation of SiAlCN during high temperature applications, the as-processed SiAlBN are subjected to oxidation in air and oxidation in pure steam at 1100C, 1200C and 1300C. Oxidation in air is carried out in a high temperature tube furnace where dry air is introduced. During steam oxidation, steam from de-ionized water, independently boiled, is introduced to high temperatures. High temperature oxidation and/or hot-corrosion will be carried out for 10, 100 and 1000 hours isothermally to examine the kinetics of materials degradation, phase transformation and the corresponding changes in materials properties for five-hole flow/pressure and hotwire sensor applications. SiAlBN specimens before and after the high temperature exposure are examined with emphasis on the surface/dimensional stability and microstructural/phase stability with respect to its sensor applications. Surface/dimensional stability are examined by investigating the formation of diffusional reaction product on the surface of SiAlCN after high temperature exposure in air and in steam using photoluminescence/raman spectroscopy (PRS), optical interferometry (OI), optical microscopy (OM), scanning electron microscopy (SEM) equipped with energy dispersive spectroscopy (EDS). Selected specimens will be analyzed in scanning/high resolution transmission electron microscopy (S/HR-TEM) with specimen preparation by focused ion beam (FIB) technique.

Phase transformations and microstructural evolution within the SiAlCN during high temperature oxidation in air and in steam are investigated by using x-ray diffraction (XRD), simultaneous thermal gravimetric analysis and differential scanning calorimetry (sTGA-DSC), OM, SEM/EDS and S/HR-TEM. Changes in electrical properties, if any, are correlated with the observed development in phases and microstructure of SiAlCN.

There are many advantages to the novel sensors based on polymer-derived ceramics incorporating SiCN, SiBCN and SiAlCN in the ceramic matrix. When incorporated into structures, such as gas turbines, that manifest harsh operating environments, the novel sensors afford accurate, real-time condition monitoring for extended periods of time. The structure housing such a sensor becomes a "smart structure" functioning with less downtime, less frequent maintenance, better utilization of material, improved safety, reliability, efficiency and provides information for design optimization.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. A process for producing a series of micro electro mechanical system (MEMS)-based sensors for high temperature flow path applications wherein sensors are fabricated with polymer derived ceramics (PDCs), comprising the steps of:
   a) selecting a polymer precursor consisting of silicon, carbon and nitrogen with excellent thermo-mechanical properties at high temperatures;
   b) incorporating in the polymer precursor a sensor for sensing point measurements in environmental conditions;
   c) incorporating in the polymer precursor a sensor for determining flow path conditions in said environmental conditions;
   d) shaping and crosslinking the polymer precursor incorporating the point measurements sensor and the flow path conditions sensor to form an infusible network of polymer components; and
   e) converting the polymer components to a polymer derived ceramic (PDC) by pyrolysis at temperatures from about 800 to about 1200° C., to provide MEMS-based sensors for use in high temperature flow path applications, that output to a recording device for accurate, real-time, on-line, in-situ condition monitoring while withstanding environmental conditions up to about 2000° K without external cooling.

2. The process of claim 1, wherein the high temperature flow path is within a structure selected from the group consisting of gas turbine, power generation plant, and turbine engine.

3. The process of claim 1, wherein the high temperature flow path is at a temperature of from about 1500° K to about 2000° K.

4. The process of claim 1, wherein the polymer-derived ceramics are fabricated using materials selected from the group consisting of SiCN, SiBCN and SiAlCN.

5. The process of claim 1, wherein the means for sensing point measurements is adapted for real-time condition monitoring.

6. The process of claim 1, wherein the output to a recording device includes a device selected from the group consisting of paper tablet, computer, compact disc, digital pen, and digital video disc.

7. The process of claim 5, wherein the real-time condition monitoring includes measurements of static and stagnation temperature and pressure.

8. The process of claim 5, wherein the real-time condition monitoring is adapted for measurements of wall heat flux.

9. The process of claim 1, wherein the polymer precursors are selected from at least one of poly[hydrazinomethylsilane] and polysilazane.

10. The process of claim 1, wherein boron and aluminum are incorporated into the polymer network to improve physical, chemical and electrical properties of the polymer-derived ceramics.

* * * * *